US008591493B2

(12) United States Patent
McGuire, Jr.

(10) Patent No.: US 8,591,493 B2
(45) Date of Patent: Nov. 26, 2013

(54) WOUND COMPRESSION DRESSING

(75) Inventor: James E. McGuire, Jr., Westerville, OH (US)

(73) Assignee: entrotech, inc., Columbus, OH (US)

( * ) Notice: Subject to any disclaimer, the term of this patent is extended or adjusted under 35 U.S.C. 154(b) by 496 days.

(21) Appl. No.: 12/911,701

(22) Filed: Oct. 25, 2010

(65) Prior Publication Data

US 2012/0101465 A1 Apr. 26, 2012

(51) Int. Cl.
*A61F 13/15* (2006.01)
*A61F 13/00* (2006.01)
*A61M 31/00* (2006.01)

(52) U.S. Cl.
USPC .................. 604/504; 604/385.01; 602/48

(58) Field of Classification Search
USPC ................ 604/385.01, 504; 602/48
See application file for complete search history.

(56) References Cited

U.S. PATENT DOCUMENTS

| | | |
|---|---|---|
| 4,984,584 A | 1/1991 | Hansen et al. |
| 5,616,387 A | 4/1997 | Augst et al. |
| 5,939,339 A | 8/1999 | Delmore et al. |
| 6,573,419 B2 | 6/2003 | Naimer |
| 2003/0040691 A1 | 2/2003 | Griesbach et al. |
| 2007/0082023 A1* | 4/2007 | Hopman et al. ............. 424/426 |
| 2008/0286576 A1 | 11/2008 | McGuire |
| 2010/0059167 A1 | 3/2010 | McGuire |

FOREIGN PATENT DOCUMENTS

WO WO-2010/048155 4/2010

OTHER PUBLICATIONS

"Smith & Nephew ALLEVYN COMPRESSION Polyurethane Dressing," http://global.smith-nephew.com/us/ALLEVYN_COMPRESSION_DRSNG_4663.html (Jan. 17, 2010).
"Release System Information Guide: Syl-Off® Solventless, Platinum-Catalyzed Vinyl Silicone Release Coatings from Dow Corning," Form No. 30-1166-01 (Dec. 21, 2007).
Essing, David, "Israeli Super Bandage Saves Lives," *IsraCast Jerusalem* (Aug. 10, 2005).
"Strength and Flexibility Make Compression Dressings Work," Stevens Urethane website: http://www.stevensurethane.com/medical/compression.html (Nov. 28, 2007).
Thomas, Stephen et al., "The Importance of Compression on Dressing Performance," http://www.worldwidewounds.com/2007/November/Thomas-Fram-Phillips/Thomas-Fram-Phillips-Compression-Wrap.html (Nov. 7, 2007).

\* cited by examiner

*Primary Examiner* — Jacqueline F. Stephens
(74) *Attorney, Agent, or Firm* — The Griffith Law Firm, A.P.C.; Lisa M. Griffith

(57) ABSTRACT

Wound compression dressings of the invention comprise: an elastic layer comprising an extensible material having recovery of greater than 90% when tested according to ASTM D412 at elongations up to about 150%; an adhesive layer on at least a portion of a first side of the elastic layer; and a release layer on at least a portion of a second side of the elastic layer opposite from the first side thereof. According to a method of providing direct compression to a wound, a wound compression dressing of the invention is provided, and the wound compression dressing is wrapped around the wound to provide the direct compression to the wound.

22 Claims, 1 Drawing Sheet

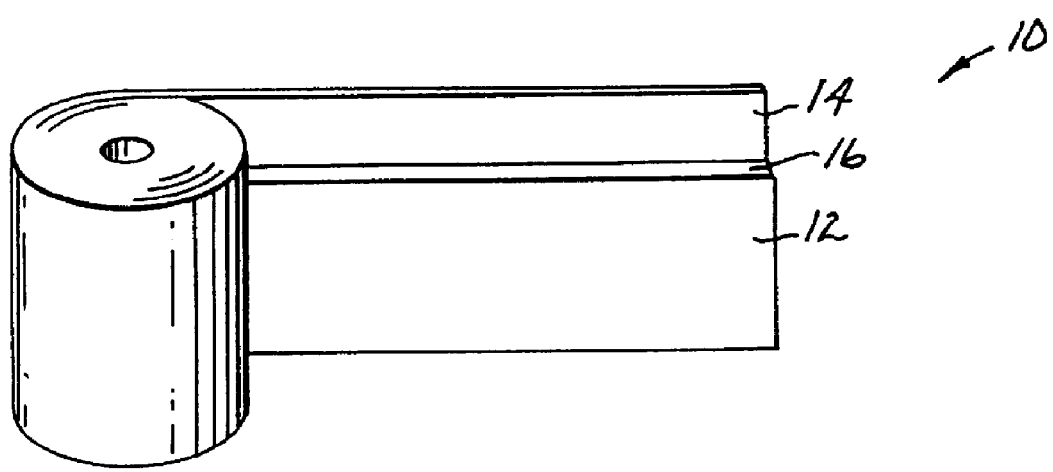

WOUND COMPRESSION DRESSING

BACKGROUND OF THE INVENTION

The present invention is directed toward wound compression dressings for control of bleeding from wounds.

Bleeding control is a major consideration in the emergency treatment of acute trauma. Rapid and effective application of compression at the scene of a traumatic incident until arrival at a medical facility has been found to significantly decrease loss of blood from wounds. As result, chances for survival of trauma victims and/or chances for avoiding a loss of their limbs are improved when compression is so applied. Traditional methods of bleeding control include those using direct compression over a wound surface, usually employing an absorbent layer, and indirect compression through application of a tourniquet, the tourniquet being tightly applied proximal to the wound.

With indirect compression, use of a tourniquet typically entails bounding an elastic material tightly around a wounded body part proximal to a wound. The tourniquet is sometimes applied with sufficient constricting force to cause ischemia distally to the site of application. While this highly effective and widely used method of bleeding control is advantageous in that it does not require an individual to apply the pressure, ischemia that can be induced thereby can be both extremely painful to the victim and even the cause of soft tissue and neurological damage to distal body parts.

Direct compression is often effective in controlling bleeding; however, direct compression is often impractical in many emergency situations due to the need for one to continually apply such pressure, often denying that individual the ability to effectively perform other tasks. Further, heavy direct compression may aggravate damage to wounded tissues and fractures and is particularly inconvenient to apply over irregularly shaped or sensitive body parts.

Alternatively, a variety of compression dressings are known for direct compression applications, many of which advantageously do not require that an individual actively administer the pressure. For example, elastic fabric wraps (e.g., those sold by 3M Co. under the COBAN and ACE trade designations) are often used as an outer layer in wound compression dressings in order to hold the inner layers in place and to apply compression to the wound. However, many elastic fabric wraps are non-adhesive and/or have inadequate recovery after being stretched around a wound, which causes them to shift with motion, compromising their comfort and compression capabilities. Therefore, such elastic fabric wraps often need to be fastened or bonded to an adhesive, which is also not ideal in that many conventionally used adhesives lose their tack when exposed to moist environments (e.g., exudates from a wound), which often leads to shifting of the dressing after its application over a wound.

Foam compression dressings available from Smith & Nephew under the ALLEVYN trade designation are described as containing a highly absorbent material embedded in a self-adherent polyurethane matrix. The dressing is covered with a waterproof polyurethane film, which film is both permeable to oxygen and water vapor as well as being bacteria-proof. The dressings are described as employing all the proven benefits of a moist wound environment without any breakdown of the dressing caused by contact with exudate. Further, the dressings are described as being slightly adherent in that they adhere well to dry, intact skin, but will not adhere to a wound's surface. The slight adherence to dry skin is stated to hold the dressing in place during application of the compression bandage. The dressings are sold in packages having multiple dressing pieces, with each piece having dimensions of 6 inches (15 cm) by 8 inches (20 cm) or in packages with multiple smaller, approximately square-shaped pieces.

U.S. Pat. No. 5,939,339 discloses a wound compression dressing described as being a porous, self-adhering, elastic bandage; an absorbent layer covering at least a portion of the self-adhering substrate; and means adapted to flexibly bond the self-adhering substrate to the absorbent layer. The bandage may be compressively wrapped around a wound and is stated to be capable of absorbing fluids and wound exudate. A preferred embodiment of the wound compression dressing therein is described as one that does not adhere to clothing, hair, or skin and that has a compressive force when extended that provides a therapeutic benefit. An elastic substrate therein is described as comprising materials that are elastic, conformable, porous, self-adhering, and that provide adequate compression. It is stated that a material made of melt blown microfiber webs may also be used as the elastic substrate. Exemplary melt blown microfiber webs are described as being a variety of well-known thermoplastic elastomers, including polyurethane, styrene-isoprene block copolymer, styrene-butadiene block copolymer, and blends of these elastomers with polyolefins such as polypropylene and polyethylene. In addition, it is stated that the melt blown microfiber webs may include, but are not limited to, staple fibers, such as rayon, polyester, nylon, cotton, LANSEAL absorbent fiber (Japan Exlan Co., Ltd.; Osaka, Japan), cellulose, or polypropylene fibers, to provide a blend of elastomeric and staple fibers. Suitable melt blown microfiber webs are described as having elongations of 30%-500% with an elastic recovery of about 90%. In order to increase the self-adherence of the dressings therein, coating both sides of the elastic substrate with a natural rubber latex or adhesive having low tack is described.

U.S. Pat. No. 6,573,419 describes an elastic adhesive wound compression dressing for control of bleeding and for dressing bleeding wounds. The wound compression dressing comprises a self-adhering, elastic bandage strip designed for, when wrapped around a body part, exerting a compressive force of between about 1 to about 180 mm Hg that is sufficient to hold the wound compression dressing in place for a period of time in order to provide a therapeutic effect to a wound. The dressing comprises an absorbent pad affixed to an inner side of a terminal portion or to a terminal end of the self-adhering, elastic bandage strip.

In a preferred embodiment described therein, the dressing comprises non-woven elastomeric fibers and/or clear polyolefin polymer or copolymer films having firm elastic extendibility in longitudinal and vertical directions and an adhesive, with the dressing having self-adhesive properties sufficient to cause two adjacent layers of the bandage to remain adhered to one another without use of a fastening mechanism. Similar to U.S. Pat. No. 5,939,339, it is stated that a material made of melt blown microfiber webs may also be used in the strip of the invention. Exemplary melt blown microfiber webs are described as being a variety of well-known thermoplastic elastomers, including polyurethane, styrene-isoprene block copolymer, styrene-butadiene block copolymer, and blends of these elastomers with polyolefins such as polypropylene and polyethylene. In addition, it is stated that the melt blown microfiber webs may include, but are not limited to, staple fibers, such as rayon, polyester, nylon, cotton, LANSEAL absorbent fiber (Japan Exlan Co., Ltd.; Osaka, Japan), cellulose, or polypropylene fibers, to provide a blend of elastomeric and staple fibers.

In another preferred embodiment of the invention described therein, the self-adhering elastic strip is constructed of a transparent material. In this manner, the dressing allows for monitoring of continued bleeding even when applied. Preferred materials are described as clear or printed polyolefin or copolymer films having both firm extendibility in the longitudinal and vertical directions and self-adhesive properties. Exemplary films include a polyethylene film consisting of 54% low-density polyethylene, 40% copolymer of ethylene and octene-1, and 6% SEBS-copolymer. This film is described as having a thickness of 100 microns, modulus at 25% elongation of 0.6 (M.D.) and 0.5 (C.D.) $Kg/mm^2$, tensile strength of 2.0 (M.D.) and 2.8 (C.D.) $Kg/mm^2$, elongation at break of 600% (M.D.) and 1,000% (C.D.), adhesion strength of 1,600 g/10 cm and adhesion to steel of 16.4 Newtons/inch. Another exemplary film described therein is that sold by the Dow Chemical Co. under the AFFINITY KC 8852 trade designation.

A need exists for alternative wound compression dressings and associated methods, particularly for use in providing direct compression over a wound. While many wound compression dressings are known, alternative dressings are desirable, factoring in certain considerations that become even more important depending on the incident scene. When the scene of a traumatic incident is a battlefield, for example, an important consideration is size and weight of the wound compression dressing that must often be transported along with other essential provisions on a combat soldier. Further, due to the inherently unstable conditions on a battlefield, ease of application and avoidance of detection by the enemy while applying the compression are important considerations. As with other applications, continued adherence of wound compression dressings over a wound and adequate compression until bleeding of the wound halts or the wounded arrives at a medical facility also continues to be an important consideration when the wound compression dressing is used on a battlefield or similar remote location.

BRIEF SUMMARY OF THE INVENTION

Wound compression dressings of the invention comprise: an elastic layer comprising an extensible material having recovery of greater than 90% when tested according to ASTM D412 at elongations up to about 150%; an adhesive layer on at least a portion of a first side of the elastic layer; and a release layer on at least a portion of a second side of the elastic layer opposite from the first side thereof. In a further embodiment, wound compression dressings of the invention exhibit greater than about 225% elongation at break when tested according to ASTM D412.

According to a method of providing direct compression to a wound, a wound compression dressing of the invention is provided, and the wound compression dressing is wrapped around the wound to provide the direct compression to the wound. Advantageously, when applied to a wound according to an exemplary embodiment, the wound compression dressing is capable of providing essentially constant compressive pressure when size of the wound decreases in an amount up to about 15% in volume as compared to when the wound compression dressing is applied to the wound initially.

Advantageously, wound compression dressings of the invention are capable of adhering both to themselves and to clothing proximate a wound in an exemplary embodiment. In one embodiment, the adhesive layer comprises a pressure-sensitive adhesive layer. In an exemplary embodiment, the adhesive layer comprises a non-sensitizing acrylic.

In one embodiment, the elastic layer is essentially impervious to moisture. In an exemplary embodiment, the elastic layer is polyurethane-based (e.g., an extrusion grade polyurethane). In another embodiment, the elastic layer comprises silicone. The elastic layer can be translucent or transparent. According to an exemplary embodiment, thickness of the elastic layer is about 50 microns (2 mils) to about 500 microns (20 mils). According to one aspect of this embodiment, thickness of the elastic layer is about 150 microns (6 mils). According to another exemplary embodiment, the elastic layer has a width of about 10 centimeters (four inches).

According to a further embodiment, the release layer comprises a material providing premium easy release properties. In yet a further embodiment, the wound compression dressing comprises an absorbent layer. Although, in another embodiment, the wound compression dressing consists essentially of the elastic layer, the adhesive layer, and the release layer.

In an exemplary embodiment, the wound compression dressing is provided in roll form. In a further embodiment, the wound compression dressing comprises a core. Advantageously, unwind noise is essentially non-existent upon unwind of a roll of the wound compression dressing in an exemplary embodiment. This is beneficial when, for example, using the wound compression dressing on a battlefield.

BRIEF DESCRIPTION OF THE SEVERAL VIEWS OF THE DRAWINGS

FIG. 1 is a perspective view of a wound compression dressing of the present invention in roll form.

DETAILED DESCRIPTION OF THE INVENTION

Wound compression dressings of the invention are laminates comprising: an elastic layer; an adhesive layer on at least a portion of a first side of the elastic layer; and, a release layer on at least a portion of a second side of the elastic layer opposite from the first side thereof. It is to be understood that each of these three laminate layers may comprise one or more individual layers. When one or more of the elastic layer, adhesive layer, and release layer comprises more than one individual layer itself, the combination of those individual layers is understood to be the "layer" formed by the individual layers.

In a preferred embodiment, if absorbent materials are desired, those are applied separately from wound compression dressings of the invention. Thus, wound compression dressings of the invention generally do not include absorbent layers according to this preferred embodiment. Preferred wound compression dressings consist essentially of the elastic layer, the adhesive layer, and the release layer. Advantageously, elimination of absorbent and other layers from the wound compression dressing minimizes volume and weight thereof, both of which are important considerations when utilizing the wound compression dressings on the battlefield or in other remote locations where one may be required to pack in their necessary provisions. As compression to stop bleeding is often the primary objective when treating wounds in remote locations as opposed to containment of any exudate from such wounds, the elimination of extraneous layers in wound compression dressings was found to be an overall improvement in those situations. Nevertheless, wound compression dressings of the invention can comprise absorbent layers and/or can be used in conjunction with absorbent materials in alternative embodiments. An exemplary absorbent material comprises QUIKCLOT COMBAT GAUZE available from Combat Medical Systems of Fayetteville, N.C.

In one embodiment, wound compression dressings of the invention are capable of adhering not only to themselves, but also to clothing and other materials that may be located between or proximate the wound and the applied wound compression dressing. Such materials are often capable of providing any absorbency desired. Advantageously, this expanded adhesion is possible without requiring an additional adhesive layer or other fastening mechanism.

In addition, as opposed to conventional elastic compression bandages that do not adhere to such materials, slippage of improved wound compression dressings on such materials is minimized according to the present invention due to this expanded adhesion and recovery of the wound compression dressing, the latter of which is discussed in more below. Furthermore, when applied to a wounded body part under moist conditions (e.g., outdoors in the rain or otherwise wet conditions or in the presence of wound exudate), the wound compression dressing is capable of forming an effective bond, displacing excess moisture as it is wound around itself, and maintaining desired adhesion and wound compression. Advantageously, smoothness and extensibility of the elastic layer, described further below, was found to assist in such displacement.

Elastic Layer

The elastic layer comprises any suitable material to provide desired properties in wound compression dressings of the invention. The elastic layer functions as a backing or intermediate substrate of the wound compression dressing, with the adhesive layer and the release layer disposed on opposite sides thereof.

Exemplary materials for use in the elastic layer include those described as being suitable for the carrier layer in U.S. Patent Publication No. US-2008-0286576, incorporated by reference herein in its entirety. Suitable base polymers for the elastic layer include, for example, polyvinyl chloride, polyvinyl acetate, polypropylene, polyester, poly(meth)acrylate, polyethylene, polyurethane, and rubbery resins (e.g., silicone elastomers).

According to one aspect of the invention, the wound compression dressing is transparent or translucent to facilitate viewing of the wound thereunder during and after its application thereon. Thus, according to one embodiment, the elastic layer comprises a relatively clear, UV-stable resin such as, for example, a silicone. According to another embodiment, the elastic layer is polyurethane-based. In addition to possessing other properties found to be desirable for use in wound compression dressings of the invention, advantageously such materials and others described as being suitable for the carrier layer in U.S. Patent Publication No. US-2008-0286576 are lightweight and cost-effective, often more so than materials used in many conventional elastic bandages for wound compression applications. Useful polyurethanes are available from Thermedics (Noveon, Inc.) of Wilmington, Mass., under the TECOFLEX trade designation (e.g., CLA-93AV) and from Bayer MaterialScience LLC of Pittsburgh, Pa., under the TEXIN trade designation (e.g., an aliphatic ester-based polyurethane suitable as a base polymer for the elastic layer and available under the trade designation, TEXIN DP7-3008).

A primary advantage of using such materials for the elastic layer is the extensibility and recovery they impart to the wound compression dressing. The terms "extensible" and "extensibility" refer to a material's ductility and its ability to be stretched and recover to essentially its original state after stretching. For example, such extensibility is evident when elongating (also referred to as stretching) the material by at least about 25%. In one embodiment, the elastic layer comprises an extensible material imparting recovery (i.e., initial length of the sample divided by length of the relaxed sample) of greater than 90% when a sample of such is stretched 25%, 50%, 100%, or 150% of its initial length according to ASTM D412. In another embodiment, the elastic layer comprises an extensible material imparting recovery of at least about 95% when tested as such. In yet a further embodiment, the elastic layer comprises an extensible material imparting recovery of at least about 99% when so tested. In still a further embodiment, the elastic layer comprises an extensible material imparting about 100% recovery when so tested. Such recovery was found to facilitate continued adherence of wound compression dressings on wounds and adequate compression thereof according to the invention. Although many conventional wound compression dressings provide adequate compression when initially applied, when the dressing shifts on the wound or when size of the wound decreases as it often does with time, the wound compression dressing often fails to provide adequate adhesion and/or wound compression as compared to those of the present invention.

Exemplary wound compression dressings of the invention are capable of maintaining constant positive pressure for compression on the wound to which they are applied due to their enhanced ability to recover after elongation. In one embodiment, wound compression dressings of the invention are capable of providing essentially constant pressure when size of the wound decreases in an amount up to about 15% in volume as compared to when the wound compression dressing is applied to a wound initially. Such a reduction in volume can arise when, for example, blood flow to a wounded's extremities is reduced as a result of the wounded undergoing circulatory shock. Advantageously, this essentially constant pressure is possible without the need to readjust the wound compression dressing or apply further direct compressive pressure over the wound after initial application of the wound compression dressing.

According to another aspect of the invention, wound compression dressings of the invention exhibit an elastic recovery force of at least about 2 N/25 mm when tested according to ASTM D5459. In a further embodiment, wound compression dressings of the invention exhibit an elastic recovery force of at least about 5 N/25 mm when tested according to ASTM D5459. In yet a further embodiment, wound compression dressings of the invention exhibit an elastic recovery force of at least about 8 N/25 mm when tested according to ASTM D5459.

According to another aspect of the invention, wound compression dressings of the invention exhibit greater than about 225% elongation at break when tested according to ASTM D412. In a further embodiment, wound compression dressings of the invention exhibit greater than about 250% elongation at break when tested as such. In a still further embodiment, wound compression dressings of the invention exhibit greater than about 300% elongation at break when tested as such. In a further embodiment still, wound compression dressings of the invention exhibit greater than about 350% elongation at break when tested as such.

Further preferable are wound compression dressings that exhibit essentially no plastic deformation when stretched according to ASTM D412 up to about 150% of their initial length. According to another aspect of the invention, wound compression dressings of the invention exhibit less than about 3% deformation after 25% elongation when tested according to ASTM D412. In a further embodiment, wound compression dressings of the invention exhibit less than about 2% deformation after 25% elongation when tested as such. In a still further embodiment, wound compression dressings of the invention exhibit less than about 1% deformation after 25% elongation when tested as such.

According to another aspect of the invention, wound compression dressings of the invention exhibit less than about 8% deformation after 50% elongation when tested according to ASTM D412. In a further embodiment, wound compression dressings of the invention exhibit less than about 5% deformation after 50% elongation when tested as such. In a still further embodiment, wound compression dressings of the invention exhibit less than about 2% deformation after 50% elongation when tested as such. In yet a further embodiment, wound compression dressings of the invention exhibit less than about 1% deformation after 50% elongation when tested as such.

According to another aspect of the invention, wound compression dressings of the invention exhibit less than about 8% deformation after 100% elongation when tested according to ASTM D412. In a further embodiment, wound compression dressings of the invention exhibit about 5% deformation or less after 100% elongation when tested as such.

Preferably, elastic layers of the invention are essentially impervious to moisture (i.e., non-porous). In order to facilitate occlusion of blood, the primary objective of wound compression dressings of the invention, use of impervious materials was found to be most effective.

Any suitable additives can be present in the elastic layer. Additives are selected as known to those skilled in the art based on the intended application. Those skilled in the art are readily able to determine the amount of such additives to use for the desired effect. For example, while the use of certain amounts of crosslinker may still allow formation of suitable wound compression dressings of the invention, if crosslinkers are present in the elastic layer, they are generally used in an amount of less than about 4 parts by weight, and preferably less than about 2 parts by weight, based on 100 parts by weight of any polymer crosslinkable therewith prior to any crosslinking reaction. Further, crosslinkers may be present if they are not used in combination with polymers that are crosslinkable therewith or where, if crosslinkable, resulting crosslink density is minimal (e.g., due to minimal reactive sites on the base polymer) so as not to significantly affect extensibility of the wound compression dressing. In a preferred embodiment, the elastic layer is essentially free of crosslinkers and reaction products thereof. As such, crosslinkers and reaction products are generally not discernible therein when using chemical analysis.

Dimensions of the elastic layer are selected according to the desired application. According to exemplary embodiments, thickness of the elastic layer is about 50 microns (2 mils) to about 500 microns (20 mils), preferably about 150 microns (6 mils).

In one embodiment, the elastic layer has a width of about 15 centimeters (six inches). This significant width was found to facilitate not only reduced bleeding, but also stabilization of bone fractures such as those of the hip. In another embodiment, the elastic layer has a width of about 5 centimeters (two inches) to about 10 centimeters (four inches). The elastic layer has a width of about 10 centimeters (four inches) in a preferred embodiment.

Adhesive Layer

The adhesive layer comprises any suitable material to provide desired properties in wound compression dressings of the invention. If desired to remove at least a portion of the dressing from the wounded body part, temporarily or permanently, the wound compression dressing is capable of being easily peeled back from itself. Further, after being so removed, the wound compression dressing is capable of effectively re-adhering in preferred embodiments. As such, it is preferred that the adhesive layer comprises a pressure-sensitive adhesive.

Still further, unlike adhesives used in conventional wound compression dressings, if any, wound compression dressings of the invention are constructed such that the adhesive layer effectively retains its tack when exposed to exudates and other moisture, obviating the need to utilize an absorbent layer to prevent slippage or unwanted shedding of the dressing due to contact with excess exudates. As such, environmental conditions in which the wound compression dressings can be effectively utilized are expanded.

According to one embodiment, the adhesive layer generally comprises a base polymer with one or more additives such as that described in U.S. Patent Publication No. US-2010-0059167-A1, incorporated herein by reference in its entirety. While any suitable chemistry can be used for the base polymer in the adhesive layer, (meth)acrylate (i.e., acrylate and methacrylate) chemistry is preferred. In particular, an adhesive based on 2-ethyl hexyl acrylate, vinyl acetate, and acrylic acid monomers polymerized as known to those skilled in the art can be used as the base polymer. However, other suitable chemistries are known to those skilled in the art and include, for example, those based on synthetic and natural rubbers, polybutadiene and copolymers thereof, polyisoprene and copolymers thereof, and silicones (e.g., polydimethylsiloxane and polymethylphenylsiloxane).

Any suitable additives can optionally be used in conjunction with the base polymer in the adhesive layer. For example, stabilizers (e.g., antioxidants, heat stabilizers, and UV-stabilizers), crosslinkers (e.g., aluminum or melamine crosslinkers), corrosion inhibitors, tackifiers, plasticizers, photocrosslinkers, colorants, fillers, and other conventional adhesive additives as known to those of ordinary skill in the art can be incorporated into the adhesive layer. If desired, an adhesion promoter may be included in the adhesive layer. However, in preferred embodiments, the material comprising the adhesive layer is selected to be chemically compatible with the elastic layer. Thus, an adhesion promoter is not required according to preferred embodiments of the invention.

Preferably, the adhesive layer is essentially free of components that may tend to migrate to its interface with the elastic layer, where such components may promote interlayer delamination. In an exemplary embodiment, the adhesive layer has less than about 0.1% residual monomer.

In a further exemplary embodiment, the adhesive layer comprises a non-sensitizing acrylic (i.e., as determined when tested in vitro based on the "International Organization for Standardization: Biological Evaluation of Medical Devices, Part 5: Test for Cytotoxicity in vitro Method" (ISO 10993-5) such as, for example, by overlaying confluent monolayers of L-929 mouse fibroblast cells with adhesive samples, incubating the same in 5% carbon dioxide for twenty-four hours at 37° C., and then examining the resulting cell cultures to determine the zone of cell lysis, if any). An exemplary adhesive comprises ECA 134, a solution acrylic pressure-sensitive adhesive available from entrochem, inc. (Columbus, Ohio).

Dimensions of the adhesive layer are selected according to the desired application. According to exemplary embodiments, thickness of the adhesive layer is about 2.5 microns (0.1 mil) to about 150 microns (6 mils), preferably about 50 microns (2 mils).

The adhesive layer may be continuous or discontinuous. According to an exemplary embodiment, width of the adhesive layer approximates width of the elastic layer. As such, in one exemplary embodiment, the adhesive layer has a width of about 15 centimeters (six inches) and, in another exemplary embodiment, the adhesive layer has a width of about 5 centimeters (two inches) to about 10 centimeters (four inches).

Release Layer

The release layer comprises any suitable material and dimensions. Exemplary release layers comprise materials conventionally used in the low adhesion backsize of a tape. In preferred embodiments, additional low surface energy materials are used for enhanced release properties. While not conventionally used in such applications, materials providing premium easy release properties are used in preferred embodiments of the present invention to decrease and often effectively eliminate noise generated when unwinding the wound compression dressing. Importantly, minimization or elimination of unwind noise facilitates stealth when using the wound compression dressing on, for example, a battlefield. Stealth is often critical in order to avoid undesired alerting of others to the wounded's location when applying a wound compression dressing to the wounded. In one embodiment, unwind noise is essentially non-existent upon unwind of a roll of the wound compression dressing of the invention. In an exemplary embodiment, when a two-inch wide release-coated sample is peel tested at an unwind speed of about 7.7 meters/minute (300 inches/minute) and 90° angle, a release force of less than about 100 grams is measured and no audible noise is observed when using such a premium easy release material.

Exemplary premium easy release materials are silicone-based. In one embodiment, such materials comprise those solventless, platinum-catalyzed vinyl silicone release materials available from Dow Corning Corporation under the SYL-OFF trade designation. A preferred release material comprises SYL-OFF 7680-010 silicone polymer available from Dow Corning Corporation.

Dimensions of the release layer are selected according to the desired application. According to exemplary embodiments, thickness of the release layer is about 0.01 micron to about 5 microns, preferably about 4 microns.

The release layer may be continuous or discontinuous. According to an exemplary embodiment, width of the release layer approximates width of the elastic layer. As such, in one exemplary embodiment, the release layer has a width of about 15 centimeters (six inches) and, in another exemplary embodiment, the release layer has a width of about 5 centimeters (two inches) to about 10 centimeters (four inches).

Form of Wound Compression Dressing

Wound compression dressings of the invention may be provided in sheet or roll form (i.e., as a tape). A roll form of one embodiment of a wound compression dressing is illustrated in FIG. 1. As illustrated therein, a wound compression dressing 10 of the invention includes an adhesive layer 12 on a first side of an elastic layer 14 and a release layer 16 on an opposite second side of the elastic layer 14. A core 18 may optionally be present when providing the wound compression dressing 10 in roll form. When present, the core 18 has any suitable dimensions. In an exemplary embodiment, a core 18 having an outer diameter of about 2.5 centimeters (one inch) is present for improved handleability of the wound compression dressing during unwind.

When provided in roll form, a pull-tab or similar mechanism may also optionally be provided for easily unwinding the dressing at the start of a roll as known to those of ordinary skill in the art.

Advantageously, as discussed above, an important consideration is size and weight of the wound compression dressing that must often be transported along with other essential provisions on a combat soldier. In exemplary embodiments of the invention, a wound compression dressing of the invention has a reduced volume of up to about 30% as compared to a conventional elastic bandage (e.g., those elastic fabric wraps sold by 3M Co. under the COBAN and ACE trade designations) of the same length and width.

EXAMPLES

Exemplary embodiments and applications of the invention are described in the following non-limiting examples.

Example 1

A wound compression dressing, commercially available from entrotech, inc. of Columbus, Ohio under the entrofilm 1134 trade designation, was tested for various properties described below. Tensile strength of the material was tested according to ASTM D412 and determined to be 70 kN/m$^2$. Elongation at break of the material was tested according to ASTM D412 and determined to be 500%. Recovery of the material was tested according to ASTM D412 and determined to be 100% when a 38 mm×13 mm (1.5 in.×0.5 in.) sample of the material was stretched 25% of its initial length, 100% when the sample was stretched 50% of its initial length, and 95% when the sample was stretched 100% of its initial length.

Additional data corresponding to elastic recovery force of the material was determined based on the test method prescribed by ASTM D5459. ASTM D5459, a standard test method for elastic recovery, permanent deformation and stress retention of stretch film, was modified in that a 25 mm×13 mm (1 in.×0.5 in.) sample of the material was stretched to 100% elongation at a cross-head speed of 1,000 mm/min. Upon reaching 100% elongation, the cross-head was maintained at that position for 5 seconds and then reversed to a point where 85% elongation was observed. The load on the sample at that point was then measured after a 60 second waiting time and recorded as the holding force. The material was measured as such to have a holding force of 8 N/25 mm.

Comparative Example C1

A self-adhesive bandage (4 inches—about 10 centimeters—wide), sold by 3M Company of St. Paul, Minn. under the COBAN trade designation, was tested for various properties described below. Tensile strength of the sample was tested according to ASTM D412 and determined to be 36 kN/m$^2$. Elongation at break of the sample was tested according to ASTM D412 and determined to be 225%. Recovery of the material was tested according to ASTM D412 and determined to be 100% when a 38 mm×13 mm (1.5 in.×0.5 in.) sample of the material was stretched 25% of its initial length, 100% when the sample was stretched 50% of its initial length, and 98% when the sample was stretched 100% of its initial length. Using the method described above with respect to Example 1, additional data corresponding to elastic recovery force of the material was determined based on the test method prescribed by ASTM D5459. The material was measured to have a holding force of 0.75 N/25 mm.

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

Further, as used throughout, ranges may be used as shorthand for describing each and every value that is within the range. Any value within the range can be selected as the terminus of the range. Similarly, any discrete value within the range can be selected as the minimum or maximum value recited in describing and claiming features of the invention.

The invention claimed is:
1. A wound compression dressing comprising:
   an elastic layer comprising an extensible material having recovery of greater than 90% when tested according to ASTM D412 at elongations up to about 150%;
   an adhesive layer on at least a portion of a first side of the elastic layer; and
   a release layer on at least a portion of a second side of the elastic layer opposite from the first side thereof.
2. The wound compression dressing of claim 1, wherein the wound compression dressing is provided in roll form.
3. The wound compression dressing of claim 2, further comprising a core.
4. The wound compression dressing of claim 2, wherein unwind noise is essentially non-existent upon unwind of a roll of the wound compression dressing.
5. The wound compression dressing of claim 1, wherein the adhesive layer comprises a pressure-sensitive adhesive layer.
6. The wound compression dressing of claim 1, wherein the adhesive layer comprises a non-sensitizing acrylic.
7. The wound compression dressing of claim 1, wherein the wound compression dressing is capable of adhering both to itself and to clothing proximate a wound.
8. The wound compression dressing of claim 1, wherein the elastic layer is essentially impervious to moisture.
9. The wound compression dressing of claim 1, wherein the elastic layer is polyurethane-based.
10. The wound compression dressing of claim 1, wherein the elastic layer comprises silicone.
11. The wound compression dressing of claim 1, wherein the elastic layer is translucent or transparent.
12. The wound compression dressing of claim 1, wherein the elastic layer comprises an extrusion grade polyurethane.
13. The wound compression dressing of claim 1, wherein when applied to a wound, the wound compression dressing is capable of providing essentially constant compressive pressure when size of the wound decreases in an amount up to about 15% in volume as compared to when the wound compression dressing is applied to the wound initially.
14. The wound compression dressing of claim 1, wherein the wound compression dressing exhibits greater than about 225% elongation at break when tested according to ASTM D412.
15. The wound compression dressing of claim 1, wherein thickness of the elastic layer is about 50 microns (2 mils) to about 500 microns (20 mils).
16. The wound compression dressing of claim 1, wherein thickness of the elastic layer is about 150 microns (6 mils).
17. The wound compression dressing of claim 1, wherein the elastic layer has a width of about 10 centimeters (four inches).
18. The wound compression dressing of claim 1, wherein the release layer comprises a material providing premium easy release properties.
19. The wound compression dressing of claim 1, further comprising an absorbent layer.
20. The wound compression dressing of claim 1, wherein the wound compression dressing consists essentially of the elastic layer, the adhesive layer, and the release layer.
21. Use of the wound compression dressing of claim 1 on a battlefield.
22. A method of providing direct compression to a wound, the method comprising:
   providing the wound compression dressing of claim 1, and
   wrapping the wound compression dressing around the wound to provide the direct compression to the wound.

* * * * *